US012714718B2

(12) United States Patent
Sebree et al.

(10) Patent No.: US 12,714,718 B2
(45) **Date of Patent: *Aug. 25, 2026**

(54) TREATMENT OF 22Q11.2 DELETION SYNDROME WITH CANNABIDIOL

(71) Applicant: Harmony Biosciences Management, Inc., Plymouth Meeting, PA (US)

(72) Inventors: Terri Sebree, Gladwyne, PA (US); Donna Gutterman, Raleigh, NC (US)

(73) Assignee: Harmony Biosciences Management, Inc., Plymouth Meeting, PA (US)

( * ) Notice: Subject to any disclaimer, the term of this patent is extended or adjusted under 35 U.S.C. 154(b) by 723 days.

This patent is subject to a terminal disclaimer.

(21) Appl. No.: 17/941,739

(22) Filed: Sep. 9, 2022

(65) Prior Publication Data

US 2023/0000792 A1 Jan. 5, 2023

Related U.S. Application Data

(63) Continuation-in-part of application No. 16/712,066, filed on Dec. 12, 2019, now Pat. No. 11,458,109.

(60) Provisional application No. 62/895,279, filed on Sep. 3, 2019, provisional application No. 62/779,591, filed on Dec. 14, 2018.

(51) Int. Cl.

| | |
|---|---|
| ***A61K 31/05*** | (2006.01) |
| ***A61K 9/06*** | (2006.01) |
| ***A61K 9/70*** | (2006.01) |
| ***A61K 31/00*** | (2006.01) |
| ***A61K 36/185*** | (2006.01) |
| ***A61P 25/24*** | (2006.01) |

(52) U.S. Cl.

CPC .............. *A61K 31/658* (2023.05); *A61K 9/06* (2013.01); *A61K 9/7038* (2013.01); *A61K 36/3482* (2024.05); *A61P 25/24* (2018.01)

(58) Field of Classification Search

CPC ...................................................... A61K 31/05

See application file for complete search history.

(56) References Cited

U.S. PATENT DOCUMENTS

| | | | |
|---|---|---|---|
| 7,423,026 | B2 | 9/2008 | Jarvinen et al. |
| 8,293,786 | B2 | 10/2012 | Stinchcomb et al. |
| 8,435,556 | B2 | 5/2013 | Stinchcomb et al. |
| 8,449,908 | B2 | 5/2013 | Stinchcomb et al. |
| 9,375,417 | B2 | 6/2016 | Smith et al. |
| 9,447,019 | B2 | 9/2016 | Mechoulam et al. |
| 9,533,942 | B2 | 1/2017 | Stinchcomb et al. |
| 9,675,656 | B2 | 6/2017 | Crowley |
| 9,730,911 | B2 | 8/2017 | Verzura et al. |
| 9,782,360 | B2 | 10/2017 | Mechoulam et al. |
| 9,943,491 | B2 | 4/2018 | De Vries et al. |
| 10,213,390 | B1 | 2/2019 | Bonn-Miller et al. |
| 10,314,792 | B2 | 6/2019 | Sebree et al. |
| 10,471,022 | B2 | 11/2019 | Bonn-Miller et al. |
| 10,555,928 | B2 | 2/2020 | Blackmon et al. |
| 10,568,848 | B2 | 2/2020 | Sebree et al. |
| 10,716,766 | B2 | 7/2020 | Aung-Din |
| 10,758,497 | B2 | 9/2020 | Bonn-Miller et al. |
| 11,458,109 | B2 * | 10/2022 | Sebree .................. A61K 31/05 |
| 12,186,282 | B2 | 1/2025 | Sebree et al. |
| 12,213,951 | B2 | 2/2025 | Sebree et al. |
| 12,226,373 | B2 | 2/2025 | Bonn-Miller et al. |
| 2008/0139472 | A1 | 6/2008 | Lauterborn et al. |
| 2010/0273895 | A1 | 10/2010 | Stinchcomb et al. |
| 2011/0052694 | A1 | 3/2011 | Stinchcomb et al. |
| 2015/0342902 | A1 | 12/2015 | Vangara et al. |
| 2015/0343071 | A1 | 12/2015 | Vangara et al. |
| 2016/0000843 | A1 | 1/2016 | Lowe et al. |
| 2016/0022627 | A2 | 1/2016 | Smith |
| 2016/0256410 | A1 | 9/2016 | Aung-Din |
| 2016/0256411 | A1 | 9/2016 | Aung-Din |
| 2016/0271252 | A1 | 9/2016 | Vangara et al. |
| 2016/0338974 | A1 | 11/2016 | Aung-Din |
| 2017/0224634 | A1 | 8/2017 | Vangara et al. |
| 2017/0231923 | A1 | 8/2017 | Guy et al. |
| 2017/0274030 | A1 | 9/2017 | Crowley |
| 2017/0348276 | A1 | 12/2017 | Bryson et al. |
| 2017/0360745 | A1 | 12/2017 | Blackmon et al. |
| 2018/0140560 | A1 | 5/2018 | De Vries et al. |
| 2019/0117619 | A1 | 4/2019 | Guy et al. |
| 2020/0188324 | A1 | 6/2020 | Sebree et al. |
| 2020/0360299 | A1 | 11/2020 | Bonn-Miller et al. |
| 2021/0196669 | A1 | 7/2021 | Bar-Lev Schleider et al. |

(Continued)

FOREIGN PATENT DOCUMENTS

| | | | |
|---|---|---|---|
| AU | 2018101357 | A4 | 10/2018 |
| CN | 105517546 | A | 4/2016 |

(Continued)

OTHER PUBLICATIONS

U.S. Appl. No. 16/737,326.
U.S. Appl. No. 17/895,008.
U.S. Appl. No. 17/942,068.
Busquets-Garcia, Arnau, et al., Targeting the endocannabinoid system in the treatment of fragile X syndrome, Nature Medicine (Mar. 2013).
International Search Report and Written Opinion of corresponding PCT/IB2019/060735, mailed Mar. 3, 2020, 12 pages.
Banks S, O'Neill C, Sebree T. Pharmacokinetic Evaluation of Subcutaneously Administered ZYN001 in Male Sprague-Dawley Rats. PainWeek. Sep. 8-12, 2015.
Bergmaschi et al., Cannabidiol Reduces the Anxiety Induced by Simulated Public Speaking in Treatment-Naiver Social Phobia Patients, Neuropsychopharmacology (2011) 36, 1219-1226.

(Continued)

*Primary Examiner* — Paul V Ward

(74) *Attorney, Agent, or Firm* — WOMBLE BOND DICKINSON (US) LLP; Danielle L. Herritt; Mark R. DeLuca

(57) ABSTRACT

The present technology relates to methods of treating one or more behavioral symptoms (for example, anxiety) of 22q11.2 deletion syndrome in a subject by administering, e.g., transdermally, an effective amount of cannabidiol (CBD) to the subject wherein one or more behavioral and/or psychiatric symptoms of 22q11.2 deletion syndrome are treated in the subject.

14 Claims, 1 Drawing Sheet

(56) References Cited

U.S. PATENT DOCUMENTS

| | | | |
|---|---|---|---|
| 2021/0369643 | A1 | 12/2021 | Sebree et al. |
| 2021/0401769 | A1 | 12/2021 | Griesser et al. |
| 2022/0096396 | A1 | 3/2022 | Sebree et al. |
| 2023/0059709 | A1 | 2/2023 | Palumbo et al. |
| 2023/0414533 | A1 | 12/2023 | Bonn-Miller et al. |
| 2024/0122873 | A1 | 4/2024 | Griesser et al. |
| 2024/0342198 | A1 | 10/2024 | Palumbo et al. |
| 2025/0134832 | A1 | 5/2025 | Sebree et al. |
| 2025/0134833 | A1 | 5/2025 | Bonn-Miller et al. |
| 2025/0177322 | A1 | 6/2025 | Bonn-Miller et al. |
| 2025/0205174 | A1 | 6/2025 | Sebree et al. |
| 2025/0288539 | A1 | 9/2025 | Sebree et al. |

FOREIGN PATENT DOCUMENTS

| | | | |
|---|---|---|---|
| CN | 107126411 | A | 9/2017 |
| GB | 2549278 | A | 10/2017 |
| WO | 2006133941 | A2 | 12/2006 |
| WO | WO-2010127033 | A1 | 11/2010 |
| WO | WO-2016109624 | A1 | 7/2016 |
| WO | 2016141056 | A1 | 9/2016 |
| WO | WO-2017068349 | A1 | 4/2017 |
| WO | WO-2017149387 | A1 | 9/2017 |
| WO | WO-2017151980 | A1 | 9/2017 |
| WO | WO-2017158539 | A1 | 9/2017 |
| WO | WO-2017178807 | A1 | 10/2017 |
| WO | WO-2017178810 | A1 | 10/2017 |
| WO | WO-2017182950 | A1 | 10/2017 |
| WO | 2018011808 | A1 | 1/2018 |
| WO | WO-2018002637 | A1 | 1/2018 |
| WO | WO-2018109471 | A1 | 6/2018 |
| WO | 2019034985 | A1 | 2/2019 |
| WO | 2019089583 | A1 | 5/2019 |
| WO | 2022017942 | A1 | 1/2022 |
| WO | 2022103638 | A1 | 5/2022 |

OTHER PUBLICATIONS

Blessing et al., Cannibidiol as a Potential Treatment for Anxiety Disorders, Neurotherapeutics, Oct. 2015, 12(4): 825-836.

Bonn-Miller M, Banks SL, Sebree T. Conversion of Cannabidiol Following Oral Administration: Authors' Response to Grotenhermen et al. Cannabis and Cannabinoid Research 2017;2:1, 5-7.

Bonn-Miller M, Gutterman D. A Permeation-Enhanced Synthetic Cannabidiol (CBD) Transdermal Gel for the Treatment of PTSD. Military Health System Research Symposium. Orlando, FL. Aug. 15-18, 2016.

Bonn-Miller M, Sebree T, O'Neill C, Messenheimer J. Neuropsychological Effects of ZYN002 (Synthetic Cannabidiol) Transdermal Gel in Healthy Subjects and Patients with Epilepsy: Phase 1, Randomized, Double-Blind, Placebo-Controlled Studies. American Epilepsy Society Annual Meeting. Houston, TX. Dec. 2-6, 2016.

Fusar-Poli, et al., "Modulation of Effective Connectivity During Emotional Processing by 49-tetrahydrocannabinol and Cannabidiol," International Journal of Neuropsychopharmacology (2010) 13, 421-432.

Gauvin D, O'Neill C, Patterson DR. Respiratory Evaluation of Subcutaneously Administered ZYN001 in Male Sprague-Dawley Rats. PainWeek. Sep. 8-12, 2015.

Jung KM, Sepers M, et al. Uncoupling of the endocannabinoid signalling complex in a mouse model of fragile X syndrome. Nat Commun 2012;3:1080.

Kidd, et al., Cannabinoids in the Treatment of Autism Spectrum Disorder: Demanding Data Before Using Fad Therapies, Pediatric Neurology, 88 (2018) 10-11.

Lozano, et al., "Advances in the Understanding of Gabaeric Neurobiology of FMR1 Expanded Alleles Leading to Targeted Treatments for Fragile X Spectrum Disorder," Curr Pharm Des Author manuscript, (2015); 21 (34): 4972-4979.

Merrick J, Lane B, Sebree T, Yaksh T, O'Neill C, Banks SL. Identification of psychoactive degradants of cannabidiol in simulated gastric and physiological fluid. *Cannabis and Cannabinoid Research* 2016;1:1, 102-112, DOI: 10.1089/can.2015.0004.

Novagant Corp. Announces Breakthrough in Cannabidiol (CBD) Transdermal Patch for Localized Delivery, Oct. 29, 2014.

O'Brien T MD, FRACP; Berkovic, S, MD, FRACP; French, J, MD, et al. Synthetic Transdermal Cannabidiol for the Treatment of Focal Epilepsy in Adults. 2017 American Epilepsy Society Annual Meeting, Washington, DC. Dec. 1-5, 2017.

Paudel KS, Hammell DC, et al. Cannabidiol bioavailability after nasal and transdermal application: effect of permeation enhancers. Drug Development and Industrial Pharmacy 2010;36(9):1088-1097.

Qin M, Zeidler Z, et al. Endocannabinoid-mediated improvement on a test of aversive memory in a mouse model of fragile X syndrome. *Behav Brain Res* Sep. 15, 2015;291:164-71.

Salgado, et al., Autism Spectrum Disorder and Cannabidiol: Have We Seen This Movie Before?, Global Pediatric Health, vol. 5:1-5 (2018).

Sativex Product Monograph, Buccal Spray, Mar. 30, 2012 (55 pages).

Sebree T, O'Neill C, Messenheimer J, Gutterman D. Safety and Tolerability of ZYN002 (Synthetic Cannabidiol) Transdermal Permeation-Enhanced Gel in Healthy Subjects and Epilepsy Patients: Three Phase 1, Randomized, Double-Blind, Placebo-Controlled Studies. American Epilepsy Society Annual Meeting. Houston, TX. Dec. 2-6, 2016.

Wei, et al., Enhancement of Anandamide-Mediated Endocannabinoid Signally Corrects Autism-Related Social Impairment, Cannabis and Cannabinoid Research, vol. 1.1 (2016).

Wheeler, et al., "Anxiety, Attention Problems, Hyperactivity, and the Aberrant Behavior Checklist in Fragile X Syndrome," American Journal of Medical Genetics, (2013) 141-155.

Winton-Brown, et al., "Modulation of Auditory and Visual Processing by Delta-9-Tetrahydrocannabinol and Cannabidiol: an fMR1 Study," Neuropsychopharmacology (2011) 36, 1340-1348.

Hadland, S., et al., "Medical Marijuana: Review of the Science and Implications for Developmental Behavioral Pediatric Practice," J Dev Behav Pediatr. 2015 ; 36(2): 115-123.

Aran, A., et al., "Cannabidiol Based Medical Cannabis in Children with Autism—a Retrospective Feasibility Study (P3.318)," Neurology, 90:15 Supplement, (2018).

Pavlovic, Zoran M., "Cannabinoids in Autism and Fragile X Syndrome: Value-Based Treatment Revolution Ahead?," Global Journal of Intellectual & Developmental Disabilities, 3(1)1-4 (Sep. 2017).

Khalil, Rami Bou, "Would some cannabinoids ameliorate symptoms of autism?", European Child & Adolescent Psychiatry, 21(4):237-238, XP035037636, ISSN: 1435-165X, DOI: 10.1007/S00787-012-0255-Z (2017).

Anonymous: History of Changes for Study: NCT02956226, "Cannabinoids for Behavioral Problems in Children with ASD (CBA)", XP055718101, Retrieved from the Internet: URL:https://clinicaltrials.gov/ct2/history/NCT02956226?V_4=View#StudyPageTop [retrieved on Jul. 27, 2020] (2017).

Hammell, D.C., et al., "Transdermal cannabidiol reduces inflammation and pain-related behaviours in a rat model of arthritis", Eur. J. Pain, vol. 20(6):936-948. doi:10.1002/ejp.818 (Jul. 2016).

Heussler, Helen et al., "A phase 1/2, open-label assessment of the safety, tolerability, and efficacy of transdermal cannabidiol (ZYN002) for the treatment of pediatric fragile X syndrome", Journal of Neurodevelopmental Disorders, vol. 11, No. 1, pp. 1-9, XP055828347 (2019).

Belmonte, Matthew K., et al., "Fragile X syndrome and autism at hte intersection of genetic and neural networks", Nature Neuroscience, vol. 9(10):1221-1225 (2006).

Hagerman, Randi, et al., "Fragile X Syndrome and Targeted Treatment Trials", National Institutes of Health Public Access Manuscript, published as Results Probl Cell Differ., vol. 54:297-335. doi:10.1007/978-3-642-21649-7_17 (2012).

Kaufmann, Walter E., et al., "Autism Spectrum Disorder in Fragile X Syndrome: Cooccurring Conditions and Current Treatment", HHS Public Access Manuscript, published as Pediatrics, vol. 139(Suppl 3):S194-S206. doi:10.1542/peds.2016-1159F (2017).

(56) References Cited

OTHER PUBLICATIONS

Pisante, S., et al., "Cannabidiol: State of the Art and New Challenges for Therapeutic Applications", Pharmacology and Therapeutics, vol. 175, pp. 133-150 (2017).
Mechoulam, Raphael, et al., "Cannabidiol: An Overview of Some Pharmacological Aspects", The Journal of Clinical Pharmacology, vol. 42, Issue 51, pp. 11S-19S (2002).
Mechoulam, Raphael, et al., "Cannabidiol—Recent Advances", Chemistry & Biodiversity; vol. 4, pp. 1678-1692 (2007).
Zynerba Pharmaceuticals Announces Top-Line Results from Phase 2 Star 1 Trial of ZYN002 in Adult Epilepsy Patients with Focal Seizures (Aug. 7, 2017).
Hagerman, Randi J., et al., "Fragile X-Associated Neuropsychiatric Disorders (FXAND)," Frontiers in Psychiatry, vol. 9. Article 564, pp. 1-9 (2018).
Crawford, Dana C., et al., "FMR1 and the Fragile X Syndrome: Human Genome Epidemiology Review," Genet. Med., Author manuscript, HHS Public Access, vol. 3(5):359-371 (2001).
Godler, David Eugeny, et al., "Methylation of novel markers of fragile X alleles is inversely correlated with FMRP expression and FMR1 activation ratio," Human Molecular Genetics, vol. 9(18): 1618-1632 (2010).
SDCAadmin, "The Difference Between Moderate to Severe Autism," Sarah Dooley Center for Autism, pp. 1-6 (2019).
Aran, Adi, et al., "Brief Report: Cannabidiol-Rich Cannabis in Children with Autism Spectrum Disorder and Severe Behavioral Problems—A Retrospective Feasibility Study," Journal of Autism and Developmental Disorders, vol. 49:1284-1288 (2019).
Hagerman, Randi J., et al., "High Functioning Fragile X Males: Demonstration of an Unmethylated Fully Expanded FMR-1 Mutation Associated with Protein Expression," American Journal of Medical Genetics, vol. 51:298-308 (1994).
International Search Report and Written Opinion of related PCT Application No. PCT/US2020/051102 mailed Dec. 18, 2020, 7 pages.
Ali, Shayma et al., "Efficacy of cannabinoids in paediatric epilepsy", Developmental Medicine & Child Neurology, vol. 61:13-18 (2019).
Kuchenbuch, Mathieu, et al., "Add-on cannabidiol significantly decreases seizures in 3 patients with SYNGAP1 developmental and epileptic encephalopathy," Epilepsia Open, vol. 5:496-500 (2020).
SynGAP Research Fund, Webinar, CBD, Seizures & SynGAP: Parents Experience (2019).
Vlaskamp, Danique R.M., et al., "SYNGAP1 encephalopathy: A distinctive generalized developmental and epileptic encephalopathy," Neurology, vol. 92(2):e96-e107 (2019).
"Lacking guidance from doctors, parents lead the charge in treating children with CBD," Peninsula Press (2018).
Salcedo-Arellano, Maria Jimena, et al., "Overlapping Molecular Pathways Leading to Autism Spectrum Disorders, Fragile X Syndrome, and Targeted Treatments", Neurotherapeutics, Springer International Publishing, Cham, vol. 18, No. 1, pp. 265-283 (2020).
International Search Report and Written Opinion for corresponding PCT/US2022/078449 mailed Feb. 2, 2023, 13 pages.
Hagerman, Paul J., Ph.D., M.D. et al., Fragile X Syndrome: Diagnosis, Treatment, and Research, The Johns Hopkins University Press, pp. 210, 213, 471 and 472, 3rd Edition (2002).
Liu, X. Shawn, et al., Rescue of Fragile X Syndrome Neurons by DNA Methylation Editing of the FRM1 Gene, Cell Press, vol. 172:979-992 (2018).
Payan Gomez, Cesar, et al., "Variable Expressivity in Fragile X Syndrome: Towards the Identification of Molecular Characteristics That Modify the Phenotype", The Application of Clinical Genetics, DovePress, vol. 14:305-312 (2021).
Clinical Leader: Zynerba Pharmaceuticals Achieves Target Enrollment in Exploratory Phase 2 Trial of ZYN002 in Fragile X Syndrome, retrieved from the internet at URL: <https://www.clinicalleader.com/doc/zynerba-pharmaceuticals-achieves-target-exploratoryphase-syndrome-0001>, retrieved on Aug. 31, 2023 (2017).
Buckner, Julia D., et al., "Cannabis-related impairment and social anxiety: the roles of gender and cannabis use motives", Addictive Behaviors, vol. 37(11):1294-1297 (2012).
Fung, Wai Lun Alan, et al., "Elevated Prevalence of Generalized Anxiety Disorder in Adults 22q11.2 Deletion Syndrome", American Journal of Psychiatry, vol. 167(8):998, XP009553437 (2010).
Siegel, Steven, et al., Transdermal Cannabidiol (CBD) Gel for the Treatment of Fragile X Syndrome (FXS), ACNP 57th Annual Meeting: Poster Session III, Neuropsychopharmacology, vol. 43, Suppl. 1, pp. S399-S400, XP093109132 (2018).
Maneeton, Narong, et al., "Risperidone for children and adolescents with autism spectrum disorder: a systematic review", Neuropsychiatric Disease and Treatment, vol. 14:1811-1820 (2018).
National Library of Medicine; Natonal Center for Biotechnology Information; PubChem; Compound Summary—Cannabidiol; 67 pages (2014).
Tartaglia, Nicole, et al., "Treatment of Fragile X Syndrome with Cannabidiol: A Case Series Study and Brief Review of the Literature", Cannabis and Cannabinoid Research, vol. 4(1):3-9 (2019).
Heussler, H. et al., "Transdermal cannabidiol (CBD) Gel for the treatment of fragile X syndrome (FXS)", 57th Annual Meeting of the American College of Neuropsychopharmacology (ACNP), Hollywood, FL. 2018, Poster P5-092, <URL: https://www.zynerba.com/wp-content/uploads/2019/05/Transdermal-Cannabidiol-CBD-Gel-for-the-Treatment-of-Fragile-X-Syndrome.pdf>.
Deng, Ming Yu, et al., "New Progress of Clinical Research to Autistic Spectrum Disorder" (DSM-5 Update).
Saul, Robert A., MD, FACMG, et al., FMR1 (FMR1-Related Disorders), Gene Reviews Japan, pp. 1-8 (2006).
Fusar-Poli, Laura et al., "Cannabinoids for People with ASD: A Systematic Review of Published and Ongoing Studies" Brain Sciences, vol. 10(572), pp. 1-18 (2020).
Extended European Search Report for corresponding EP22803457.5 dated Oct. 22, 2025, 5 pages.
Agarwal, Rumi et al., "Current state of evidence of cannabis utilization for treatment of autism spectrum disorders", BMC Psychiatry, vol. 19(328):1-10 (2019).
Protic, Dragana et al., "New Targeted Treatments for Fragile X Syndrome", Current Pediatric Reviews, vol. 15, pp. 251-258.
Thom, Robyn, P. et al., "Recent Updated in Psychopharmacology for the Core and Associated Symptoms of Autism Spectrum Disorder", Current Psychiatry Reports, vol. 23(79):1-9 (2021).
Yamasue, Hidenori et al., Emerging pharmacological therapies in fragile X syndrome and austim, Current Opinion, www.co-neurology.com, vol. 32(4):635-640 (2019).
Fleury-Teixeiran, Paulo, et al., "Effects of CBD-Enriched Cannabis sativa Extract on Autism Spectrum Disorder Symptoms: An Observational Study of 18 Participants Undergoing Compassionate Use", Front. Neurol., vol. 10 (2019) https://doi.org/10.3389/fneur.2019.01145.

* cited by examiner

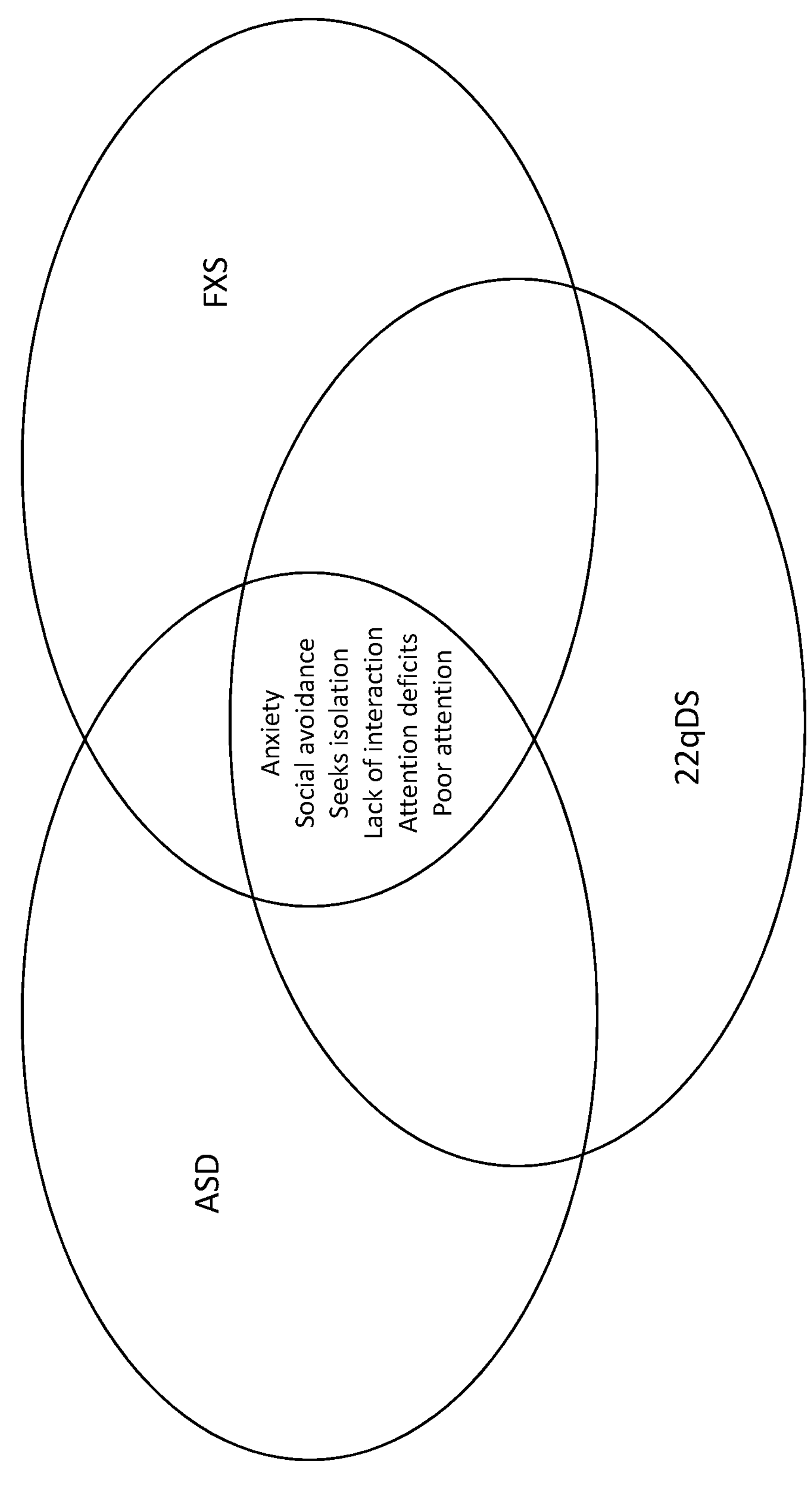
FXS
22qDS
ASD
Anxiety
Social avoidance
Seeks isolation
Lack of interaction
Attention deficits
Poor attention

TREATMENT OF 22Q11.2 DELETION SYNDROME WITH CANNABIDIOL

CROSS REFERENCE TO RELATED APPLICATIONS

This application is a continuation-in-part of U.S. patent application Ser. No. 16/712,066 filed Dec. 12, 2019, which claims the benefit of and priority to U.S. Provisional Application No. 62/779,591 filed Dec. 14, 2018 and U.S. Provisional Application No. 62/895,279 filed Sep. 3, 2019. The contents of each of which are hereby incorporated herein in their entirety.

FIELD OF THE TECHNOLOGY

The present disclosure relates to methods of treating one or more behavioral and/or psychiatric symptoms (for example, anxiety, irritability) of 22q11.2 deletion syndrome in a subject by administering an effective amount of cannabidiol (CBD) to the subject wherein one or more behavioral and/or psychiatric symptoms of 22q11.2 deletion syndrome are treated in the subject.

BACKGROUND

Cannabinoids are a class of chemical compounds found in the *Cannabis* plant. The two primary cannabinoids contained in *Cannabis* are cannabidiol, or CBD, and 49-tetrahydrocannabinol, or THC. CBD lacks the psychoactive effects of THC. Studies have shown that CBD can be used to treat disorders such as epilepsy, arthritis, and cancer.

22q11.2 deletion syndrome is caused by a hemizygous microdeletion of chromosome 22. The deletion of chromosome 22 occurs near the middle of the chromosome at a location designated as q11.2. The deletion results in the poor development of several body systems. The symptoms associated with 22q11.2 deletion syndrome vary in both the number of symptoms that are present in a human suffering from 22q11.2 deletion syndrome as well as the severity of each symptom. Prominent neuropsychiatric and phenotypic features include heart defects, poor immune system function (which can lead to recurrent infections), a cleft palate, complications related to low levels of calcium in the blood, and delayed development with both emotional and behavioral issues, cognitive impairment, anxiety, ADHD, and development of psychosis in late adolescent or early adulthood.

Children with 22q11.2 deletion syndrome can have developmental delays, which can include delayed speech, growth and learning disabilities. These developmental delays can cause behavioral and psychiatric symptoms such as irritability, social isolation, and anxiety. “Later in life, they are at an increased risk of developing mental illnesses such as schizophrenia, depression, anxiety, and bipolar disorder.” (Genetics Home Reference, U.S. National Library of Medicine, 22q11.2 deletion syndrome, https://ghr.nlm.nih.gov/condition/22q112-deletion-syndrome.)

SUMMARY

The present disclosure relates to a method of treating one or more behavioral and/or psychiatric symptoms of 22q11.2 deletion syndrome in a subject. The method includes administering an effective amount of cannabidiol (CBD) to the subject wherein one or more behavioral symptoms of 22q11.2 deletion syndrome are treated in the subject. Administering the CBD includes transdermally or orally administering.

In some embodiments, the CBD is (−)- CBD. The effective amount of CBD can be between about 50 mg to about 1000 mg daily. In some embodiments, the effective amount of CBD is initiated at about 50 mg daily and titrated up to about 500 mg daily dose or about 1000 mg daily. The effective amount of CBD can be initiated at about 50 mg daily and titrated up to about 250 mg daily. In some embodiments, the effective amount of CBD is initiated at 250 mg daily. The effective amount of CBD can be initiated at 500 mg daily. In some embodiments, the 500 mg daily dose and the 1000 mg daily dose is administered to patients that weigh greater than 35 kg. The CBD can be administered in a single daily dose or in two daily doses. In some embodiments, the effective amount of CBD can be 390 mg in divided daily doses.

The CBD can be formulated as a gel or an oil. In some embodiments, the CBD is formulated as a permeation-enhanced gel. The gel can contain between 1% (wt/wt) CBD to 7.5% (wt/wt) CBD. In some embodiments, the gel contains 4.2% (wt/wt) CBD. In some embodiments, the gel contains 7.5% (wt/wt) CBD.

In some embodiments, the transdermal preparation can be a cream, a salve or an ointment. The CBD can be delivered by a bandage, pad or patch.

Alleviating one or more behavioral and/or psychiatric symptoms of 22q11.2 deletion syndrome can include treating or alleviating general anxiety. Anxiety is the symptom that caregivers of children with 22q11.2 deletion syndrome found the most burdensome and desired treatment to relieve the anxiety, which can improve overall quality of life.

Other symptoms that can be alleviated include psychosis, mood disorders, emotional and behavioral issues, and/or attention-deficit/hyperactivity disorder (ADHD).

The CBD can be administered transdermally on the subject’s upper arm and shoulder. In some embodiments, the CBD is administered transdermally on the subject’s thigh or back.

The CBD can be synthetic CBD. The CBD can be purified CBD. The CBD can be botanically derived.

In some embodiments, transdermally administering an effective amount of cannabidiol (CBD) can reduce an intensity of at least one adverse event or side effect relative to orally administering CBD. The at least one adverse event or side effect can be a gastrointestinal (GI) adverse event. The at least one adverse event or side effect can be liver function. In some embodiments, the at least one adverse event is somnolence. In some embodiments, the frequency and intensity of somnolence is reduced as an adverse event.

BRIEF DESCRIPTION OF THE DRAWINGS

FIG. 1 is a Venn diagram showing the common behavioral features of ASD, FXS, and 22q11.2 deletion syndrome, according to an illustrative embodiment of the technology.

DETAILED DESCRIPTION

As used herein, the term “treating” or “treatment” refers to mitigating, improving, relieving, or alleviating at least one symptom (such as a behavioral symptom) of a condition, disease or disorder in a subject, such as a human, or the improvement of an ascertainable measurement associated with a condition, disease or disorder.

As used herein, the term "clinical efficacy" refers to the ability to produce a desired effect in humans as shown through a Food and Drug Administration (FDA), or any foreign counterparts, clinical trial.

As used herein, the term "cannabidiol" or "CBD" refers to cannabidiol; cannabidiol prodrugs; pharmaceutically acceptable derivatives of cannabidiol, including pharmaceutically acceptable salts of cannabidiol, cannabidiol prodrugs, and cannabidiol derivatives. CBD includes, 2-[3-methyl-6-(1-methylethenyl)-2-cyclohexen-1-yl]-5-pentyl-1,3-benzenediol as well as to pharmaceutically acceptable salts, solvates, metabolites (e.g., cutaneous metabolites), and metabolic precursors thereof. The synthesis of CBD is described, for example, in Petilka et al., *Helv. Chim. Acta,* 52:1102 (1969) and in Mechoulam et al., *J. Am. Chem. Soc.,* 87:3273 (1965), which are hereby incorporated by reference.

As used herein, the term "transdermally administering" refers to contacting the CBD with the patient's or subject's skin under conditions effective for the CBD to penetrate the skin.

The Drug Product ZYN002 is a transdermal cannabidiol (CBD) gel. CBD is the primary non-euphoric cannabinoid in the *Cannabis sativa* L plant. The CBD contained within ZYN002 is a pharmaceutically produced Active Pharmaceutical Ingredient (API) that is chemically identical to the CBD present in *Cannabis.*

CBD has a modulating effect on the endocannabinoid system and may help restore synaptic homeostasis by acting as a negative allosteric modulator of $CB_1$, thereby attenuating $CB_1$ receptor overstimulation, internalization, and desensitization. Moreover, CBD has effects on $serotonin_{1A}$ signal transduction, $GABA_A$ receptor signaling, and dopamine $D_2$ and $D_3$ receptor signaling, which may contribute to beneficial effects in patients with 22q.11.2 deletion syndrome. The expectation of a wide margin of safety in humans was founded on the results of well-controlled studies in which CBD has exhibited high tolerability across several modes of administration.

ZYN002 is being developed as a clear, transdermal gel to provide consistent, controlled cannabidiol (CBD) delivery with twice daily (every 12 hours [Q12 H]) dosing. Because CBD is virtually insoluble in water, ethanol and propylene glycol are used as solubilizing agents and diethylene glycol monoethyl ether (brand name: Transcutol® HP) is used as a permeation enhancer.

22q11.2 deletion syndrome (also referred to as 22qDS) is caused by a hemizygous microdeletion of chromosome 22. The deletion of chromosome 22 occurs near the middle of the chromosome at a location designated as q11.2. The deletion results in the poor development of several body systems. The most common symptoms of 22q11.2 deletion syndrome are heart defects (74% of individuals), abnormalities with the development of the palate (69% of individuals), characteristic facial features (elongated face, almond-shaped eyes, wide nose, and small ears), learning difficulties (70-90% of individuals) including significant delay in the development of language (70% will have minimal words by 24 months of age), and immune system problems.

22q11.2 deletion syndrome is the most common (yet under-diagnosed) microdeletion syndrome affecting 1 in 2,000 to 1 in 4,000 live births. Approximately 50 genes are affected resulting in effects on multiple body systems. 22q11.1DS is inherited as autosomal dominant but 90-95% cases are spontaneous (McDonald-McGinn et al, "22q11.2 deletion syndrome" Nat Rev Dis Primers; 1:15071.doi: 10.1038/nrdp.2015.71, 2015). Patients usually harbor a 1.5 to 3 Mb hemizygous deletion at chromosome 22q11.2, resulting in pathognomonic T-Box Protein 1 (TBX1), adaptor protein CRKL and/or mitogen-activated protein kinase 1 (MAPK1) haplo-insufficiency.

The clinical presentations of 22q11.2 deletion syndrome are highly variable within and between families, even in identical twins. Each patient presents their own unique profile of symptoms and signs. Males and females are equally affected. Undiagnosed older children and adults are often only ascertained due to behavioral problems or school performance. In some cases, adults are only diagnosed when they have an affected child. Over 180 clinical features have been described in association with 22q11.2 deletion syndrome, none of which in isolation is considered pathognomonic for the condition (Koczkowska et al, "Genomic findings in patients with clinical suspicion of 22q11.2 deletion syndrome" Journal Appl Genetics 2017 58:93-98).

The most common medical problems include congenital heart defects (primarily conotruncal abnormalities such as Tetralogy of Fallot), facial and palatal abnormalities, immunodeficiency, and hypocalcemia. There is a very wide range in the severity of these effects from life threatening to very minimal or symptomatic and undiagnosed. The neurocognitive profile is highly variable (both inter- and intra-individual). Typically, early in infancy motor delays (hypotonia) and speech and language delays are evident. The majority of patients fall into an IQ range of 70 to 84. These patients are also at an increased risk to develop ADHD, autism spectrum disorder (ASD), anxiety and mood disorders as well as psychotic disorders and schizophrenia. This complex behavioral/psychiatric phenotype changes across ages particularly with the risk of development of schizophrenia (Swillen, "Developmental Trajectories in 22q11.2 deletion" Am J Med Genet C Semin Med Genet June 2015).

In children, developmental delays are common, including mild intellectual delay and/or learning disability with an average IQ around 70.

The present disclosure relates to a method of treating one or more behavioral and/or psychiatric symptoms of 22q11.2 deletion syndrome in a subject by administering an effective amount of cannabidiol (CBD) to the subject wherein one or more behavioral symptoms of 22q11.2 deletion syndrome are treated in the subject. Administering the effective amount of CBD includes transdermally or orally administering.

The present disclosure also relates to a method of treating a human suffering from 22q11.2 deletion syndrome by administering a therapeutically effective amount of synthetic or purified cannabidiol to the human suffering from the 22q11.2 deletion syndrome to effectively treat the 22q11.2 deletion syndrome in the human in need thereof. The cannabidiol can be administered transdermally or orally.

CBD has a modulating effect on the endocannabinoid system, agonist effect on $serotonin_{1a}$ receptors, and positive allosteric modulator at $GABA_A$ receptors. Transdermal or oral administration of an effective amount of CBD gel can be an effective treatment for the behavioral and/or psychiatric phenotypes of 22q11.2 deletion syndrome, for example, anxiety.

Anxiety in individuals can disrupt development and quality of life of individuals suffering from 22q11.2 deletion syndrome more than IQ. Anxiety, not IQ, can predict the adaptive functioning of individuals with 22q11.2 deletion syndrome. Controlling anxiety in children, for example, in children six-years old to adolescent, the development of psychosis can be prevented or delayed. Addressing anxiety and mental health issues in patients with 22q11.2 deletion syndrome can improve quality of life of these individuals.

Other symptoms that can be treated include psychosis, mood disorders, emotional and behavioral issues, and/or attention-deficit/hyperactivity disorder (ADHD).

In some embodiments, transdermal delivery of cannabinoids (e.g., CBD) has benefits over oral dosing because it allows the drug to be absorbed through the skin directly into the bloodstream. This avoids first-pass liver metabolism, potentially enabling lower dosage levels of active pharmaceutical ingredients with a higher bioavailability and improved safety profile. Transdermal delivery also avoids the gastrointestinal tract, lessening the opportunity for GI related adverse events and the potential degradation of CBD by gastric acid into THC, which can be associated with unwanted psychoactive effects. Moreover, transdermal delivery of CBD reduces the intensity and frequency of somnolence adverse events, which are typically present in oral dosing of CBD. Transdermal delivery of CBD can avoid liver function adverse events, which are typically present in oral dosing of CBD. In some embodiments, transdermally administering an effective amount of CBD reduces an intensity of at least one adverse event by about 15% to about 95% relative to orally administering CBD.

The CBD can be in a gel form and can be pharmaceutically-produced as a clear, permeation-enhanced gel that is designed to provide controlled drug delivery transdermally or orally with once- or twice-daily dosing. The CBD gel can be between 1% (wt/wt) CBD to 7.5% (wt/wt) CBD. The CBD gel can have, for example, 4.2% (wt/wt) CBD or 7.5% (wt/wt) CBD). The CBD gel can be applied topically by the patient or caregiver to the patient's upper arm and shoulder, back, thigh, or any combination thereof. The CBD can be applied orally by the patient, the caregiver, or a combination thereof.

The CBD gel can include diluents and carriers as well as other conventional excipients, such as wetting agents, preservatives, and suspending and dispersing agents.

The CBD gel can include a solubilizing agent, a permeation enhancer, a solubilizer, antioxidant, bulking agent, thickening agent, and/or a pH modifier. The composition of the CBD gel can be, for example, a. cannabidiol present in an amount of about 0.1% to about 20% (wt/wt) of the composition; b. a lower alcohol having between 1 and 6 carbon atoms present in an amount of about 15% to about 95% (wt/wt) of the composition; c. a first penetration enhancer present in an amount of about 0.1% to about 20% (wt/wt) of the composition; and d. water in a quantity sufficient for the composition to total 100% (wt/wt). Other formulations of the CBD gel can be found in International Publication No. WO 2010/127033, the entire contents of which are incorporated herein by reference.

The effective amount of CBD can be between about 50 mg to about 1000 mg daily, which can be administered in a single daily dose or twice daily dosing.

Example 1: Common Behavioral Features of Autism, Fragile X Syndrome, and 22q11.2 Deletion Syndrome Autism Spectrum Disorder (ASD), Fragile X Syndrome (FXS), 22q11.2 deletion syndrome are complex neurodevelopmental conditions with considerable overlap in neuropsychological and behavioral symptomatology. ASD is characterized by problems in social communication and social interaction, as well as restricted and repetitive patterns of behavior, interests, or activities. FXS is a rare genetic condition caused by CGG repeat expansion in the FMR1 (fragile X mental retardation 1) gene located on the X chromosome; behavioral symptoms can include social withdrawal, anxiety, avoidance of eye contact, sensory hypersensitivity, echolalia, and hand flapping. 22q11.2 deletion syndrome is one of the most common microdeletion syndromes and often involves behavioral symptoms of social limitations and difficulty in maintaining relationships with peers.

The socio-behavioral deficits seen in ASD and FXS have been attributed to dysregulation of the endocannabinoid systems, which is comprised of (1) two G-protein-coupled receptors (a) cannabinoid receptor type 1 ($CB_1$), located primarily in the CNS and (b) cannabinoid receptor type 2 ($CB_2$), located in multiple systems throughout the body; and (2) endogenous cannabis-like ligands (endocannabinoids) that bind to $CB_1$ receptors and modulate synaptic transmission throughout the CNS; the two best described are anandamide (AEA) and 2-arachidonoylglycerol (2-AG).

Cannabidiol (CBD) is a non-euphoric cannabinoid. CBD has a modulating effect on the endocannabinoid system, agonist effect on $serotonin_{1a}$ receptors, and positive allosteric modulator at $GABA_A$ receptors. Transdermal or oral administration of an effective amount of CBD gel can be an effective treatment for the behavioral and/or psychiatric phenotypes of 22q11.2 deletion syndrome, for example, anxiety.

Objective: The objective of this study was to conduct a retrospective literature review on patients with ASD, FXS, and 22q11.2 deletion syndrome to determine the nature and extent of symptomatic overlap in these conditions and to suggest a possible role for CBD in the management of these shared symptoms based on insights from an open-label, 12-week study evaluating the safety, tolerability and initial efficacy of transdermal CBD for the treatment of behavioral and emotional symptoms associated with child/adolescent FXS. (Heussler et al., *A phase ½, open-label assessment of the safety, tolerability, and efficacy of transdermal cannabidiol (ZYN002) for the treatment of pediatric fragile X syndrome*; J. Neurodev Disorder. 2019; 11(1): 16)

Methods: A search of the PubMed database was conducted using the terms "behavior," "behavioral symptoms," "autism spectrum disorder," "ASD," "Fragile X Syndrome," "FXS," "22q11.2 deletion syndrome," "parents," "caregivers," and "CBD and treatment of anxiety" with no restriction on date or publication type. Records were analyzed for relevance.

Results

All Conditions: The most common behavioral manifestations across all conditions are anxiety-related; such as social avoidance, irritability, attention deficits, stereotypy, poor communication, and social unresponsiveness. See FIG. 1, Common Behavioral Features of ASD, FXS, and 22q11DS.

ASD: Anxiety-related symptoms are common in patients with ASD, with up to 84% of children experiencing some degree of debilitating anxiety; rates of physician-diagnosed anxiety disorders range from 42-55% and may include simple phobias, generalized anxiety disorder, separation anxiety disorder, obsessive-compulsive disorder, and social phobias. Comorbid anxiety disorders can be broad-ranging and associated with behaviors such as aggression/irritability and isolation from same-age peers. Inattention and hyperactivity are often present in Attention Deficit-Hyperactivity Disorder and ASD, and they are common to their respective diagnostic criteria. Children with ASD who have severe intellectual disability ([ID] IQ<40) showed higher levels of psychiatric symptoms (anxiety, mood, sleep, organic syndromes, and stereotypies/tics) than those with ID but no ASD.

FXS: In FXS, severe cognitive and social impairments are more common in males than in females. FXS usually has profound effects on the life of patients (comorbid conditions, social impairment) as well as their caregivers and families (mental health, absence from work/school). Anxiety and social avoidance are considered core features of FXS. Social avoidance has been defined as a behavioral response to anxiety that arises from fear of social interaction; thus, anxiety can be thought of as a foundational precipitant to social avoidance. Social avoidance encompasses behaviors that may include seeking isolation (e.g., stay in their room to avoid others), lack of interaction, social escape (e.g., face-hiding, leaning away), and gaze avoidance that distance the individual from his/her social counterparts. Variation in FMR1 protein expression has been linked to avoidance behaviors among females with the disorder. In a study that used interviews of parents/caregivers (n=97) of boys and girls with FXS to determine the prevalence of anxiety (based on DSM-IV criteria), 82.5% of participants had at least 1 anxiety disorder, irrespective of sex, age, presence of autism, or IQ, with the most common diagnoses being specific phobia (59.6%); social phobia (58.3%); selective mutism (25.3%); generalized anxiety disorder (23.7%); and obsessive-compulsive disorder (23.7%). The presence of ID in patients with FXS impairs their ability to self-report symptoms of worry and fear, increasing reliance on caregiver observations of outward behavioral manifestations of anxiety characteristics, which may include any of the following: social avoidance; nervous behavior during social situations; shyness; refusal of activities with social demands; poor understanding of social cues from inattention to faces, socioemotional processing, social skills during interpersonal interactions; fearfulness; social escape behaviors.

22q11.2 deletion syndrome: The most common behavioral/psychiatric diagnoses in children with 22q11.2 deletion syndrome are ADHD, ASD, and anxiety. A large-scale, collaborative study (>1400 participants aged 6-68 yrs) reported ADHD in 37% of 6-12 year-olds and in nearly 24% of 13-17 year-olds; ASD peaked in 13-17 year-olds (25.4%); anxiety disorders were more prevalent than mood disorders at all ages, but especially in children and adolescents with at least 33% of 6-17 year-olds reporting anxiety disorder. Up to one-third of patients with 22q11.2 deletion syndrome will develop schizophrenia and schizo-affective disorder by late adolescent and early adulthood, and over 40% of patients have been reported to a schizophrenic spectrum disorder after 25 years of age. Although these diagnoses are reported in individuals with 22q11.2 deletion syndrome, the diagnosis of ASD is particularly controversial in this population and may be related to poor clinical understanding of the typical behavioral and/or psychiatric phenotype. The emergence of social deficits during adolescence can represent a major source of disability in some individuals with 22q11.2 deletion syndrome; cross-sectional studies show that children with 22q11.2 deletion syndrome are withdrawn and shy and have social impairments which may be less of a concern to the individual.

Role of CBD: CBD has diverse pharmacologic effects. Based on findings from an open-label study in children/adolescents with FXS (Heussler et al., *A phase ½, open-label assessment of the safety, tolerability, and efficacy of transdermal cannabidiol* (*ZYN*002) *for the treatment of pediatric fragile X syndrome*; J. Neurodev Disorder. 2019; 11(1): 16) and a retrospective literature review, CBD may improve multiple symptoms experienced by patients with ASD, FXS, and 22q11.2 deletion syndrome, and it is generally well tolerated in children and adults. Results from receptor pharmacology studies investigating the possible role of CBD in the treatment of behavioral symptoms associated with ASD, FSX, and 22q11.2 deletion syndrome suggest (1) a role for the endocannabinoid system in regulating behavioral symptoms and (2) the pharmacology of CBD is broad, continues to be defined, and may prove beneficial in addressing important symptoms. Findings from the first crossover trial testing the effects of CBD on symptoms of social anxiety in adults with social phobia found significant and clinically meaningful reductions in both physiological and cognitive indicators of anxiety, which may translate to therapeutic effects in patients with ASD, FXS, and 22q11.2 deletion syndrome. A recent case series provided initial evidence that CBD may lead to broad improvement in childhood FXS symptomology, including symptoms of anxiety and social avoidance. An open-label, 12-week study evaluated the safety, tolerability and initial efficacy of transdermal CBD for the treatment of behavioral and emotional symptoms associated with child/adolescent FXS and found both positive effects on the emotional and behavioral symptoms of FXS, including for many, an increase in social confidence which may be translatable to the other defined populations.

Conclusions: Patients with ASD, FXS, and 22q11.2 deletion syndrome share a constellation of socio-behavioral symptoms that includes anxiety, leading to seeking isolation behavior (social avoidance), irritability, attention deficits, and poor communication. Preliminary evidence shows that CBD improves social anxiety and associated behavioral manifestations suggesting that CBD may prove to be effective in managing the spectrum of behavioral symptoms associated with these conditions.

Example 2: An Open-Label, Tolerability and Efficacy Study of ZYN002 Administered as a Transdermal Gel to Children and Adolescents with 22q11.2 Deletion Syndrome Objectives: The primary objective was to evaluate the safety and tolerability of ZYN002 administered as a transdermal gel formulation in patients ages 6 to <18 years, in the treatment of 22q11.2 Deletion Syndrome. The secondary objective was to evaluate the efficacy of ZYN002 in the treatment of symptoms of 22q11DS.

Methodology: This was an open-label study to assess the safety, tolerability and efficacy of CBD administered as ZYN002, a transdermal gel, for the treatment of child and adolescent patients with 22q11.2 deletion syndrome. Male and female patients with 22q11.2 deletion syndrome were treated in Period 1 for 14 weeks with 250 mg and 500 mg of CBD (patients ≤35 kg received 250 mg CBD daily; patients >35 kg received 500 mg CBD daily). For patients with less than a 25% improvement from baseline in the ABC-C irritability subscale, the investigator could increase the total daily dose at Week 6 of treatment. Twenty male and female patients, ages 6 to <18 years, received ZYN002.

During screening procedures, the following assessments were administered:

Aberrant Behavior Checklist (ABC-C)

Autism Diagnostic Observation Schedule®-2 (ADOS®-2) (Note: was not administered at Screening if it had been administered in the prior 6 months and the results were available) Clinical Global Impression-Severity (CGI-S)

Anxiety, Depression and Mood Scale (ADAMS)
Qualitative Caregiver Reported Behavioral Problems Survey
Pediatric Anxiety Rating Scale (PARS)

The following questionnaires and scales were administered during the trial:

ABC-C
CGI-S
Clinical Global Impression-Improvement (CGI-I) (not completed on Visit 2, Day 1)
ADAMS
Qualitative Caregiver Reported Behavioral Problems Survey (not completed at Visit 2)
PARS Aberrant Behavior Checklist-Community (ABC-C): The Aberrant Behavior Checklist-Community, 2nd Edition, was completed by the parent/caregiver, with support from the site staff. The ABC-C asks responders to rate behaviors from "0—not at all a problem" to "3—the problem is severe in degree" across 58 questions. Use of the checklist has been validated in a variety of clinical populations.

Anxiety, Depression, and Mood Scale (ADAMS): The Anxiety, Depression, and Mood Scale was completed by the parent/caregiver, with support from the site staff. The ADAMS was used as a comprehensive assessment of anxiety, depression, and mood among the patients. The ADAMS is comprised of 28 items, which are rated on a scale of "0—not a problem" to "3—severe problem." The ADAMS yields a total score as well as five subscale scores: "Manic/Hyperactive Behavior," "Depressed Mood," "Social Avoidance," "General Anxiety," and "Compulsive Behavior."

Clinical Global Impressions Scale-Improvement: The Clinical Global Impression Scale, Improvement (CGI-I), is commonly used in clinical trials as they allow the clinician to utilize the history from the caregiver and incorporate the score into a clinical rating for the severity of symptoms. CGI-I is a 7-point scale that is used to assess how much the patient's behavioral symptoms associated with 22q11.2 deletion syndrome have improved, or worsened, relative to a baseline assessment at the beginning of the treatment. The scores are rated as: 1—very much improved; 2—much improved; 3—minimally improved; 4—no change; 5—minimally worse; 6—much worse; or 7—very much worse.

Pediatric Anxiety Rating Scale (PARS): The PARS is a clinician-rated caregiver interview that covers 61 behaviors related to anxiety (Riddle M A, et al, The Pediatric Anxiety Rating Scale (PARS) Development and Psychometric Properties, J. Am. Acad. Child Adolesc. Psychiatry, 2002, 4(9): 1061-1069). The PARS provides broad coverage of separation anxiety, social phobia, and generalized anxiety. Symptoms are further categorized into Social Interactions or Performance Situations, Separation, Generalized, Specific Phobia, Panic Symptoms/Physical Signs, Obsessive-Compulsive, Health/Illness Concerns, and Other. The interviewer assesses the severity by quantifying the frequency and degree of interference and avoidance in family, school and community settings. Each of seven severity items is scored on a scale of 1 to 5, with 5 being the most severe and frequent. The final score is the sum of five of the seven severity items. The five-item scale is recommended for use during treatment studies (Riddle et al. 2002).

Safety Monitoring: Patient safety was monitored at each study visit using standard measures, including physical and neurological exams, examination of skin at application sites for irritation, vital signs, 12-lead ECGs, the C-SSRS, safety laboratory tests, and AE monitoring.

Number of Patients (Planned): Twenty male and female patients were enrolled.

Select Inclusion Criteria: Male or female children and adolescents aged 6 to <18 years, at the time of Screening. Enrolled patients had a diagnosis of 22q11.2 deletion syndrome confirmed by genetic testing, with or without autistic features. Patients had a CGI-S score of 4 or higher at Screening Visit 2. Patients had a score of the ABC-C Irritability Subscale of 18 or higher at Screening and Visit 2. Patients with a history of seizure disorders were currently receiving treatment with a stable regimen of one or two AEDs, or were seizure-free for one year if not currently receiving AEDs.

Treatment Period: This study had a 14-Week Treatment Period as follows:

- Patients weighing ≤35 kg received 125 mg CBD applied Q12H (±2 hours); total daily dose of 250 mg CBD. Each application consisted of one sachet of ZYN002 CBD 4.2% concentration, containing 2.98 g of gel. At Week 6, if the patient had less than a 25% improvement from baseline in the ABC-C irritability subscale, the investigator increased the dose as follows:
  - Patients who weigh ≤35 kg receiving a total daily dose of 250 mg CBD had their daily dose increased to 500 mg. Each application consisted of two sachets of ZYN002 CBD 4.2% concentration, containing 2.98 g of gel.
- Patients >35 kg received 250 mg CBD applied Q12H (±2 hours); total daily dose of 500 mg CBD. Each application consisted of two sachets of ZYN002 CBD 4.2% concentration, each sachet containing 2.98 g of gel. At Week 6, if the patient had less than a 25% improvement from baseline in the ABC-C irritability subscale, the investigator increased the dose as follows:
  - Patients who weigh >35 kg receiving a daily dose of 500 mg CBD increased the daily dose to 750 mg. Each application consisted of three sachets of ZYN002 CBD 4.2% concentration, containing 2.98 of gel.

Duration of Treatment: Parents/caregivers applied the study drug twice daily for up to 14 weeks.

Statistical Methods: Descriptive statistics (mean, median, standard deviation, minimum, and maximum) for continuous data and number (n) and percentage (%) for categorical data were determined for all efficacy and safety parameters.

Safety assessments (actual and change from screening) were summarized using descriptive statistics and presented by maintenance dose.

Results ABC-C: Results from the ABC-C tests are summarized in Tables 1-3. In Table 1 the ABC-C results at Week 6, compared to baseline, are presented.

TABLE 1

| Subscale | Mean/Median Baseline Score | Week 6 Mean/Median Score | Week 6 Change from Baseline | Week 6 Mean/Median % Improvement | P Value |
|---|---|---|---|---|---|
| Hyperactive Noncompliance | 18.2/14.0 | 12.9/9.0 | −5.4/−5.0 | −16.9/−38.5 | 0.0033 |
| Irritability | 18.7/19.0 | 12.4/11.0 | −6.3/−5.0 | −31.3/−32.9 | 0.0017 |
| Inappropriate | 4.0/4.0 | 2.4/2.0 | −1.6/−1.0 | −40.2/−33.3 | 0.0030 |

TABLE 1-continued

| Subscale | Mean/Median Baseline Score | Week 6 Mean/Median Score | Week 6 Change from Baseline | Week 6 Mean/Median % Improvement | P Value |
|---|---|---|---|---|---|
| Speech | | | | | |
| Stereotypic Behavior | 4.4/2.0 | 2.9/1.0 | −1.4/0.0 | −34.4/−50.0 | 0.0275 |
| Social Withdrawal | 15.5/11.0 | 10.1/9.0 | −5.4/−5.0 | −32.6/−45.5 | 0.0046 |

In Table 2 the ABC-C results at Week 14, compared to baseline are presented. The baseline score was adjusted at Week 14 due to subjects leaving the clinical trial before Week 14.

TABLE 2

| Subscale | Mean/Median Baseline Score | Week 14 Mean/Median Score | Week 14 Change from Baseline | Week 14 Mean/Median % Improvement | P Value |
|---|---|---|---|---|---|
| Hyperactive Noncompliance | 18.1/13.5 | 10.4/7.0 | −7.6/−6.0 | −16.5/−38.1 | 0.0091 |
| Irritability | 18.4/19.0 | 10.0/9.0 | −8.4/−5.5 | −36.3/−39.6 | 0.0055 |
| Inappropriate Speech | 4.2/4.0 | 2.4/2.0 | −1.8/−2.5 | −18.3/−50.0 | 0.0166 |
| Stereotypic Behavior | 3.9/2.0 | 1.6/1.0 | −2.3/−1.0 | −52.1/−58.3 | 0.0155 |
| Social Withdrawal | 14.4/10.5 | 7.9/4.5 | −6.4/−4.0 | −27.6/−46.4 | 0.0110 |

In Table 3 a summary of the number (%) of subjects showing an overall improvement, at Week 6 and Week 14, for each subscale is presented.

TABLE 3

| Subscale | Week 6 Improvement >= 25% | Week 6 Improvement >= 35% | Week 14 Improvement >= 25% | Week 14 Improvement >= 35% |
|---|---|---|---|---|
| Hyperactive | Yes: 10 (58.8%) | Yes: 9 (52.9%) | Yes: 10 (62.5%) | Yes: 8 (50.0%) |
| Noncompliance | No: 7 (41.2%) | No: 8 (47.1%) | No: 6 (37.5%) | No: 8 (50.0%) |
| Irritability | Yes: 11 (68.8%) | Yes: 6 (37.5%) | Yes: 10 (62.5%) | Yes: 9 (56.3%) |
| | No: 5 (31.3%) | No: 10 (62.5%) | No: 6 (37.5%) | No: 7 (43.8%) |
| Inappropriate | Yes: 12 (70.6%) | Yes: 8 (47.1%) | Yes: 12 (75.0%) | Yes: 11 (68.8%) |
| Speech | No: 5 (29.4%) | No: 9 (52.9%) | No: 4 (25.0%) | No: 5 (31.3%) |
| Stereotypic | Yes: 8 (47.1%) | Yes: 8 (47.1%) | Yes: 9 (56.3%) | Yes: 9 (56.3%) |
| Behavior | No: 9 (52.9%) | No: 9 (52.9%) | No: 7 (43.8%) | No: 7 (43.8%) |
| Social | Yes: 11 (64.7%) | Yes: 11 (64.7%) | Yes: 10 (62.5%) | Yes: 10 (62.5%) |
| Withdrawal | No: 6 (35.3%) | No: 6 (35.3%) | No: 6 (37.5%) | No: 6 (37.5%) |

Results ADAMS: Results from the ADAMS are summarized in Tables 4 and 5. In Table 4 the ADAMS results at Week 6, compared to baseline, are presented.

TABLE 4

| Subscale | Mean/Median Baseline Score | Week 6 Mean/Median Score | Week 6 Change from Baseline | Week 6 Mean/Median % Improvement | P Value |
|---|---|---|---|---|---|
| Total Score | 36.5/35.0 | 24.4/21.0 | −12.2/−8.0 | −30.8/−37.0 | 0.0011 |
| General Anxiety | 10.2/9.0 | 6.5/5.0 | −3.6/−3.0 | −34.1/−33.3 | 0.0008 |
| Depressed Mood | 7.5/5.0 | 4.1/4.0 | −3.4/−2.0 | −42.3/−50.0 | 0.0018 |
| Social Avoidance | 9.3/8.0 | 6.1/5.0 | −3.2/−3.0 | −17.6/−35.4 | 0.0241 |
| Obsessive Compulsive Behavior | 3.2/3.0 | 2.1/1.0 | −1.1/−1.0 | −30.3/−42.9 | 0.0475 |

TABLE 4-continued

| Subscale | Mean/Median Baseline Score | Week 6 Mean/Median Score | Week 6 Change from Baseline | Week 6 Mean/Median % Improvement | P Value |
|---|---|---|---|---|---|
| Manic Hyperactive Behavior | 7.6/7.0 | 6.3/6.0 | −1.3/−2.0 | −13.9/−14.3 | 0.0079 |

In Table 5 the ADAMS results at Week 14, compared to baseline are presented. The baseline score was adjusted at Week 14 due to subjects leaving the clinical trial before Week 14.

TABLE 5

| Subscale | Mean/Median Baseline Score | Week 14 Mean/Median Score | Week 14 Change from Baseline | Week 14 Mean/Median % Improvement | P Value |
|---|---|---|---|---|---|
| Total Score | 36.1/32.0 | 17.7/18.0 | −18.4/−12.0 | −45.3/−43.0 | 0.0005 |
| General Anxiety | 10.4/10.0 | 5.1/4.5 | −5.4/−3.5 | −43.6/−48.8 | 0.0005 |
| Depressed Mood | 7.6/6.5 | 3.4/3.0 | −4.3/−3.5 | −50.3/−52.8 | 0.0033 |
| Social Avoidance | 8.7/7.5 | 4.3/2.5 | −4.4/−3.0 | −41.3/−50.0 | 0.0084 |
| Obsessive Compulsive Behavior | 3.0/2.5 | 1.1/1.0 | −1.9/−2.0 | −64.0/−66.7 | 0.0037 |
| Manic Hyperactive Behavior | 7.6/6.5 | 4.4/4.5 | −3.1/−2.5 | −38.2/−27.4 | 0.0032 |

Results CGI-I: Results from the CGI-I tests are summarized in Table 6. In Table 6 the CGI-I scores at Week 6 and Week 14 are compared to baseline.

TABLE 6

| | Week 6 (N = 17) | Week 14 (N = 16) |
|---|---|---|
| IMPROVED (Total) | 14 (82.4%) | 12 (75%) |
| Very Much Improved | 0 | 0 |
| Much Improved | 6 (35.3%) | 10 (62.5%) |
| Improved | 8 (47.1%) | 2 (12.5%) |
| NOT IMPROVED (Total) | 3 (17.6%) | 4 (25%) |
| No Change | 3 (17.6%) | 2 (12.5%) |
| Minimally Worse | 0 | 2 (12.5%) |
| Much Worse | 0 | 0 |
| Very Much Worse | 0 | 0 |

Results PARS: Results from the PARS tests are summarized in Table 7

TABLE 7

| | Mean/ Median Baseline Score | Week 14 Mean/ Median Score | Week 14 Change from Baseline | Week 14 Mean/ Median % Improvement | P Value |
|---|---|---|---|---|---|
| Total Score | 15.0/15.0 | 8.5/9.0 | −6.2/−6.0 | −40.6/−40.0 | 0.0005 |

Results Summary: The use of CBD for the treatment of behavioral and/or psychiatric symptoms of patients with 22q11.2 Deletion Syndrome showed improvement in caregiver and clinician assessments. The total score and all five subscales of the ADAMS tests showed statistically significant improvements at Week 6 and Week 14 to treatment compared to baseline. All five subscales of the ABC-C tests showed statistically and clinically meaningful improvements at Week 6 and Week 14 compared to baseline. The PARS showed statistically significant improvements at Week 14 compared to baseline. The majority of patients showed clinically meaningful improvements at Week 6 and Week 14 as demonstrated by the CGI-I tests. Seventy-five percent of patients were rated by clinicians as “improved”, “much-improved” or “very much improved” with nearly two-thirds (62.5%) of the patients being “much improved” or “very much improved”. The transdermal administration of CBD was well tolerated. These results show that real reductions in general anxiety, social withdrawal and social avoidance, in children and adolescents with 22q11.2 deletion syndrome can be achieved through administration of CBD.

Unexpectedly, significant and clinically meaningful improvements in ADAMS Obsessive/Compulsive Behavior and were observed. In the publication of Kayser et al. “Acute Effects of Cannabinoids on Symptoms of Obsessive-Compulsive Disorder: A Human Laboratory Study” *Depress Anxiety* (2020) 37(8), pp. 801-811 (Kayser), the researchers conclude that “that smoked cannabis, whether containing primarily THC or CBD, has little acute impact on OCD symptoms and yields smaller reductions in anxiety compared to placebo.” In light of the Kayser publication, it was unexpected to see the improvements in OCD behaviors.

What is claimed is:

1. A method of treating irritability in a subject diagnosed with 22q11.2 deletion syndrome, the method comprising:

administering an effective amount of cannabidiol (CBD) to the subject wherein irritability is treated in the subject, wherein the effective amount is sufficient to show an improvement in irritability, as determined by an Aberrant Behavior Checklist—Community (ABC-C) irritability subscale assessment, compared to a baseline assessment of irritability, as determined by ABC-C, at the beginning of treatment.

2. The method of claim 1, wherein the CBD is (−)- CBD.

3. The method of claim 1, wherein the effective amount of CBD is between about 50 mg and about 1000 mg total daily.

4. The method of claim 1, wherein the effective amount of CBD is about 250 mg total daily.

5. The method of claim 1, wherein the effective amount of CBD is about 500 mg total daily.

6. The method of claim 1, wherein the effective amount of CBD is about 750 mg total daily.

7. The method of claim 1, wherein the CBD is formulated as a gel.

8. The method of claim 7, wherein the CBD is formulated as a permeation-enhanced gel.

9. The method of claim 1, wherein the CBD is administered in a single daily dose.

10. The method of claim 1, wherein the CBD is administered in two daily doses.

11. The method of claim 1, wherein the CBD is transdermally.

12. The method of claim 1, wherein the CBD is a synthetic CBD.

13. The method of claim 1, wherein the CBD is botanically derived.

14. The method of claim 1, wherein the CBD is purified.

* * * * *